United States Patent [19]

Gramer

[11] Patent Number: 5,776,916
[45] Date of Patent: Jul. 7, 1998

[54] MEDICAMENT FOR REDUCING THE INTRAOCULAR PRESSURE

[76] Inventor: Eugen Gramer, An den Muhltannen 16, D-8700 Wurzburg, Germany

[21] Appl. No.: 478,182

[22] Filed: Jun. 7, 1995

Related U.S. Application Data

[63] Continuation of Ser. No. 961,678, filed as PCT/EP91/01295, Jul. 10, 1991, abandoned.

[30] Foreign Application Priority Data

Jul. 10, 1990 [DE] Germany .................. 40 21 885.6

[51] Int. Cl.⁶ .................................................. A61K 31/685

[52] U.S. Cl. ........................................... 514/78; 514/913
[58] Field of Search ................................. 514/78, 913

[56] References Cited

PUBLICATIONS

Physician's Desk Reference for Ophthamology. 16 Edition 1988. pp. 3 and 11.

*Primary Examiner*—Zohreh Fay
*Attorney, Agent, or Firm*—John F. A. Earley; John F. A. Earley, III; Harding, Earley, Follmer & Frailey

[57] ABSTRACT

A medicament for reduction of intraocular pressure comprises both carbachol and a locally applicable betablocker.

20 Claims, No Drawings

MEDICAMENT FOR REDUCING THE INTRAOCULAR PRESSURE

This is a continuation of application Ser. No. 07/961,678, filed as PCT/EP91/01295, Jul. 10, 1991 now abandoned.

DESCRIPTION

The invention refers to a medicament for local application in the eye (carbachol-betablocker combination preparation) only 2×times daily for reduction of pathologically elevated intraocular pressure in cases of glaucoma.

The new combination preparation of carbacol can also be used as part of a four-component medication therapy on account of its unrestricted compatibility with dipivalyl epinephrine (DPE). A portion of the four-component therapy can, for example, consist of a combination of a betablocker with a moitic, either as separate preparations or as a combined preparation, e.g. in the combination of betablocker and pilocarpine or betablocker and carbachol. Betablockers reduce the separation of aqueous humor while the miotic improves the ease of drainage.

Our own investigations have revealed that if a carbachol-betablocker combination (carbachol eyedrops 3% 4×daily and betablockoer 0.5% 2×daily) (baseline) is combined with a preparation combining dipivalyl epinephrine and guanethidine then surprisingly there is an augmented additive pressure reduction effect of 4 mm Hg on the 2nd day after additional treatment with the DPE combination preparation. Aas a result of pharmacological sympathectomy guanethidine (Thilodigon®) leads to a sensitization of the adrenaline receptors and, hence, to an augmentation of the effect of the DPE.

This therapeutic scheme, that would be of utility in achieving maximum pressure reduction in difficult to control glaucomas has until now required 3 bottles of medication, whereby carbachol has to be applied 4×daily, the betablocker 2×daily and Thilodigon 2×daily. This therapy scheme is, therefore, only of limited application on account of compliance problems while a betablocker-carbachol combination preparation requiring application only 2×daily remains unavailable. The combination preparation suggested, comprising carbachol and betablocker, simplifies the four-component therapy to: carbachol-betablocker combination preparation 2×daily (bottle No. 1) and Thilodigon® eyedrops (bottle No 2) 1×daily or 2×daily.

A miotic combination preparation has been available until now containing pilocarpine 2% and metipranolol 0.1% (Normoglaucon®), but this has to be applied 4×daily. A miotic-betablocker combination preparation with a constant pressure reduction of 12 hours in the instillation curve so that it only requires application 2×daily and whose betablocker component is unrestrictedly compatible with dipivalyl epinephrine (DPE) has not previously been described.

The ideal miotic-betablocker combination preparation must fulfill the following conditions:

1. twice daily application
2. unrestricted compatibility with DPE and DPE combination preparations and
3. as low a concentration as possible of the betablocker component (with 2×daily application)

Hence, the purpose of the invention is to make available a medicament (carbachol and betablocker combination preparation) whose administration causes a greater decrease in the intraocular pressure than can be achieved by use of the individual preparations, whereby:

the handling is simpler (application only 2×daily instead of 4×daily plus 2×daily)

there is reduced danger on account of false application (only one bottle; reduction of the total quantity of active ingredient and preservative with equivalent pressure-reducing effect on account of altered pharmacokinetics and pharmaceutical formulation as a fixed combination; attack prophylaxis on account of preponderant miotic effect)

there is a reduction of side effects (reduction of variations in visual acuity, reduction of exposure to preservatives and of the total quantity of active ingredient)

and there is simultaneous unrestricted compatibility with all other active ingredients and particularly with DPE or combinations containing DPE.

Fundamentally any locally applied betablocker can be employed in this new combination preparation of carbachol and betablocker, and that is combined with carbachol in the possible dose levels of 0.75%, 1.5%, 2.25% and 3%. A carbachol-betaxolol combination preparation is regarded as being prerequisite for unlimited compatibility with DPE and DPE combination preparations. In the case of unselective betablockers their use in conjunction with preparations containing DPE would lead to a partial loss of the activity of DPE.

Carbachol, a synthetic choline derivative, only differs from acetylcholine in that the acetyl group has been replaced by a carbamyl group. This results in a double effect. It acts as a direct parasympathicomimetic and as a cholinesterase inhibitor. It is these pharmacokinetics that make this well-known substance of interest as a component in a miotic-betablocker combination that for the first time allows only 2×daily application and exhibits appreciable advantages over the pilocarpine-betablocker combination, (e.g. Normoglaucon®).

On account of the short duration of the effect of pilocarpine 2% a combination of the betablocker with pilocarpine 2% in aqueous solution requires a high dosage scheme involving 4 applications daily. Application 4 times daily involves a greater risk of allergization, the chronic application of pilocarpine leads to a greater exposure to preservatives and also to an increased danger of creating subsensitivity to pilocarpine. The pronounced double effect of carbachol results in the duration of its effect being appreciably longer; thus it is known that carbachol 3% used as a single preparation has an effect lasting 12 hours which corresponds to that of pilocarpine 2% eye ointment. The magnitude of the reduction in intraocular pressure brought about by carbachol 3% eyedrope is equivalent to that achieved by pilocarpine 8% eyedrops. The prolonged action and increased pressure reduction of carbachol 3% eyedrops is therefore more likely to allow reduction of the dosage scheme to 2×daily than would the use of pilocarpine 2%. This means that the therapy scheme is more easily fitted into the patient's particular daily routine and this leads to a considerable improvement in the quality of life for the patient.

The combination of carbachol and betaxolol into a single preparation has a longer-lasting effect and causes a greater reduction in pressure than the use of the substances as two separate preparations. Hence the mechanism of action of the combination preparation does not appear to be merely the sum of the individual mechanisms of the separate preparations. This is a surprising effect for which no proven pharmacological explanation has been found.

The extended period of action of the combination preparation cannot simply be explained in terms of a reduction of the mutual washout effects, but rather points to a change in the pharmacokinetics and/or another interaction of the medicaments within the eye. The reduction of the flow of aqueous humor by the betablocker component allows the carbachol component, that acts as a direct parasympathicomimetic and as a cholesterase inhibitor, to exert its effect for a longer period.

The suggested novel combination preparation comprising betaxolol 0.25% suspension or betaxolol 0.5% solution in combination with carbachol eyedrops 3% (for the solution) and a lower concentration when the suspension is employed, has a pH of 6.9 and exhibits good stability without the necessity for an expensive two-compartement bottle. The effect of carbachol is dose-dependent. Carbachol 3% solution alone causes a significant reduction in the intraocular pressure lasting for more than 8 hours. When carbachol in suspension is incorporated in a combination preparation with betaxolol it is able to produce the same reduction in intraocular pressure. It has been found that when the betablocker component is in suspension it is possible to obtain an identical reduction in intraocular pressure while reducing the concentration by almost one half, i.e. the use of 0.28% betaxolol with the suspension technology achieves an identical result to that obtained with 0.5% betaxolol solution. A single application of 1.5% carbachol solution makes it possible to achieve constant miosis for almost 24 hours. Variations in visual acuity are, therefore, expected to be less pronounced with the carbachol combination than with the pilocarpine combination. The use of the suspension technology allows the reduction of local and systemic side effects since the bolus character of application of both the betablocker and the carbachol is reduced by the delayed release of active ingredient. The reduction of the quantity of active ingredient by the application of the suspension technology (reduction of the concentration by almost one half in the case of the betablocker and reduction of the concentration in thp case of the carbachol preparation) and the additional reduction in the frequency of instillation to 2×daily provides the combination preparation with a higher safety profile with respect to systemic side effects. The extent to which the concentration of carbachol can be reduced by the use of suspension technology while retaining the intraocular pressure reduction obtainable with carbachol 3% solution is being investigated at the present time with, amongst other things, animal experiments in Cynomoglus monkeys. The choice of the betablocker betaxolol not only results in reduced pulmonary side effects but also endows the new carbachol-betaxolol combination preparation with better combining properties with other groups of active ingredients. Nonspecific betablockers do not abolish the improvement in drainage brought about by adrenaline, but they can reduce it, while in animal experiments in primates the beta 1 specific blocker betaxolol has been found not to affect the action of DPE when applied as a separate preparation. This means that betaxolol-carbachol combination preparations are more compatible with DPE and DPE-containing preparations when multicomponent therapy is indicated in connection with very high intraocular pressures.

The decisive advantage of the suggested carbachol-betaxolol combination is that 2×daily application only is required in the case of both the aqueous solution and the suspension. The use of suspension technology involving poly(styrene-divinylbenzene)sulfonic acid (Amberlite IRP-69) 2.5 mg as medicament carrier and Carbomer 934 P 2 mg to increase the depot function (ALCON patent) leads to the same reduction of intraocular pressure while retaining the 2×daily application scheme. It is an innovation in this combination preparation that the suspension technology is employed for the first time for carbachol for the improvement of penetration for carbachol too.

Hence, on the basis of previous knowledge it would seem appropriate in the case of the combination preparation in solution to employ both carbachol and betablocker at their highest nationally (or regionally) permitted concentrations, while in the case of the suspension technology betaxolol S 0.28% and carbachol 3% or carbachol S 1.5% should be preferred. The double effects of carbachol as direct parasympathicomimetic and as cholinesterase inhibitor are advantages for combination with betablockers, e.g. with betaxolol, in the same preparation, the hydrophilic properties of carbachol which can, incidentally, be improved by the preservative benzalkonium chloride as well as by the suspension technology are probably one reason why the surprisingly favorable properties of carbachol have not previously been exploited in preparations combining other active ingredients.

What is claimed:

1. A medicament for reducing intraocular pressure comprising a therapeutically effective amount of the fixed combination of carbachol and a locally applicable betablocker.

2. A medicament according to claim 1, the medicament taking the form of eye drops, eye ointment, eye gel, eye insert or other medicament carriers according to the suspension technology for local application in the eye.

3. A medicament of claim 1,
   wherein the carbachol is present at a therapeutic concentration of 0.5 to 4% and the betablocker is present at a therapeutic concentration of 0.1 to 2%.

4. The medicament of claim 3, wherein carbachol is present at the therapeutic concentration of 3% and the betablocker at the therapeutic concentration of 0.1 to 2%.

5. The medicament of claim 3, the betablocker being betaxolol S 0.28%.

6. The medicament of claim 3, the betablocker being betaxolol solution 0.5%.

7. The medicament of claim 4, the betablocker being betaxolol S 0.28%.

8. The medicament of claim 4, the betablocker being betaxolol solution 0.5%.

9. The medicament of claim 3, the concentration being carbachol S 1.5% and betablocker 0.1–2%.

10. A medicament for reducing intraocular pressure, wherein carbachol and a locally applicable betablocker are present,
    the carbachol being carbachol S 1.5%,
    the betablocker being betaxolol S 0.28%, and
    the medicament taking the form of eye drops, an eye ointment, an eye gel, or an eye insert.

11. A medicament for reducing intraocular pressure comprising a therapeutically effective amount of the fixed combination of carbochol and a locally applicable betablocker, wherein carbochol is present at the therapeutic concentration of 3% and the betablocker is present at the therapeutic concentration of 0.5%.

12. The medicament of claim 11, the betablocker being a beta-1 blocker.

13. The medicament of claim 12, the betablocker being betaxolol solution 0.5%.

14. The medicament of claim 12, the betablocker being betaxolol S 0.28%.

15. The medicament of claim 11, the betablocker being a non-selective beta-1-beta-2 blocker.

16. The medicament of claim 15, the betablocker being timolol solution 0.5%.

17. The medicament of claim 11, the medicament taking the form of eye drops, eye ointment, eye gel, eye insert or other medicament carriers according to the suspension technology for local application in the eye.

18. The medicament of claim 9, the concentration being betaxolol S 0.28%.

19. The medicament of claim 3, the betablocker being a non-selective beta-1-beta-2 blocker.

20. The medicament of claim 3, the betablocker being a beta-1 blocker.

* * * * *